United States Patent
Yu et al.

(10) Patent No.: US 11,123,308 B2
(45) Date of Patent: Sep. 21, 2021

(54) COMPOSITION CONTAINING CANNABIDIOL AND/OR CANNABIDIVAROL AND APPLICATION THEREOF IN TREATMENT OF DYSMENORRHEA

(71) Applicant: HANYI BIO-TECHNOLOGY COMPANY LTD., Beijing (CN)

(72) Inventors: Zhaohui Yu, Beijing (CN); Ke Zhang, Beijing (CN); Xin Tan, Beijing (CN)

(73) Assignee: HANYI BIO-TECHNOLOGY (BEIJING) CO., LTD., Beijing (CN)

( * ) Notice: Subject to any disclaimer, the term of this patent is extended or adjusted under 35 U.S.C. 154(b) by 0 days.

(21) Appl. No.: 16/646,533

(22) PCT Filed: Aug. 16, 2018

(86) PCT No.: PCT/CN2018/100835
§ 371 (c)(1),
(2) Date: Mar. 11, 2020

(87) PCT Pub. No.: WO2019/052303
PCT Pub. Date: Mar. 21, 2019

(65) Prior Publication Data
US 2020/0261376 A1  Aug. 20, 2020

(30) Foreign Application Priority Data
Sep. 15, 2017 (CN) .......................... 201710835129.8

(51) Int. Cl.
| | | |
|---|---|---|
| *A61K 31/05* | (2006.01) | |
| *A61P 15/00* | (2006.01) | |
| *A61F 13/472* | (2006.01) | |
| *A61K 9/70* | (2006.01) | |
| *A61L 15/20* | (2006.01) | |
| *A61L 15/44* | (2006.01) | |
| *A61F 13/47* | (2006.01) | |

(52) U.S. Cl.
CPC ............ *A61K 31/05* (2013.01); *A61F 13/472* (2013.01); *A61K 9/7023* (2013.01); *A61L 15/20* (2013.01); *A61L 15/44* (2013.01); *A61P 15/00* (2018.01); *A61F 2013/4708* (2013.01); *A61L 2300/216* (2013.01)

(58) Field of Classification Search
CPC ........ A61P 15/00; A61P 29/02; A61F 13/472; A61F 2013/4708; A61L 15/20; A61L 15/44; A61L 2300/216; A61K 9/70; A61K 31/352; A61K 9/127; A61K 31/05; A61K 9/06; A61K 9/7023; A61K 2300/00
See application file for complete search history.

(56) References Cited

U.S. PATENT DOCUMENTS

2016/0256411 A1* 9/2016 Aung-Din ................. A61P 1/08

OTHER PUBLICATIONS

Hill et al. ("Cannabidivarin-rich cannabis extract are anticonvulsant in mouse and rat via a CB1 receptor-independent mechanism" in British Journal of Pharmacology, (2013), 170, pp. 679-692). (Year: 2013).*
Jiaqi Huang and Biyuan Zhuang (CN 202288641 U, published Jul. 4, 2012, Machine Translated document) (Year: 2012).*

* cited by examiner

*Primary Examiner* — Blessing M Fubara
(74) *Attorney, Agent, or Firm* — Platinum Intellectual Property LLP

(57) ABSTRACT

The present invention discloses a composition for preventing and/or treating woman dysmenorrhea; the composition includes cannabidiol and/or cannabidivarol, a penetration enhancer as well as a carrier; the mass ratio of the cannabidiol and/or the cannabidivarol to the penetration enhancer is 1:(0.1-0.8). The composition provided by the present invention can effectively relieve woman dysmenorrhea, and solve the problem of lackness of a composition of cannabidiol and/or cannabidivarol which can effectively prevent and/or treat woman dysmenorrhea in the prior art. Meanwhile, the composition provided by the present invention can also be used in preparation of a feminine hygiene product for preventing and/or treating woman dysmenorrhea.

13 Claims, No Drawings

COMPOSITION CONTAINING CANNABIDIOL AND/OR CANNABIDIVAROL AND APPLICATION THEREOF IN TREATMENT OF DYSMENORRHEA

RELATED APPLICATIONS

This application is a United States National Stage Application filed under 35 U.S.C 371 of PCT Patent Application Serial No. PCT/CN2018/100835, filed Aug. 18, 2018, which claims Chinese Patent Application Serial No. CN 201710835129.8, filed Sep. 15, 2017, the disclosure of all of which are hereby incorporated by reference in their entirety.

FIELD

The present invention relates to a composition containing cannabidiol and/or cannabidivarol, and particularly relates to application of the composition containing cannabidiol and/or cannabidivarol in preparation of an externally applied drug and a feminine hygiene product for preventing and/or treating woman dysmenorrhea.

BACKGROUND

Dysmenorrhea is a common gynecological disease and a frequently-occurring disease, it has many causes of disease, its pathogenesis is complicated, repeatability is high, and dysmenorrhea is hard to treat, especially it is more common in unmarried female and young girls during menarche, it is manifested as periodical lower abdominal distending pains, crymodynia, burning pains, stabbing pains, dull pains, bearing-down pains, colicky pains, spasmodic pains, and tearing pains during a menstrual period or before and after menorrhea, the pains extend to the lumbosacral back, even involving thighs and feet, even accompanied with systemic symptoms, thereby seriously influencing work and study of women, and decreasing quality of life.

In clinical experience, traditional Chinese medicine takes "dispersing stagnated liver qi for relieving qi stagnation, dredging the channels, promoting blood circulation and removing blood stasis, regulating qi and relieve a pain" as a therapy theory, the patients take a decoction for treatment, however, the decoction is bitter and tends to produce a side effect. Western medicine commonly uses analgesics or hormones in treatment of dysmenorrhea, but the analgesics may cause adverse outcomes such as dysfunction of a nervous system, memory loss, and insomnia. The hormones may make human body have dependency, and may cause disorder of human hormone metabolism.

Cannabidiol (CBD) is extracted from a natural plant hemp, and has effects of convulsion resisting, sedation and hypnosis, anxiety resisting, psychosis resisting, inflammation resisting and neuroprotection, and has no mental effect, and the binding ability of CBD with CB1 and CB2 receptors is lower than that of tetrahydrocannabinol (THC). In 2015, GW pharmaceutical corporation of USA developed an intravenous injection by using CBD, this medication has obtained orphan drug qualification granted by U.S. Food and Drug Administration (FDA), and can be used in treatment of hypoxic ischemic encephalopathy of newborn (NHIE).

Patent CN103025325A discloses application of plant cannabinoid cannabidivarol (CBDV) in treatment of epilepsy, and this prior art discloses that a hemp plant extract for treatment of epileptic seizure contains at least 50% (w/w) of plant cannabinoid, and contains CBDV as primary plant cannabinoid and CBD as secondary cannabinoid.

Patent CN1976690A discloses a pharmaceutical composition for treating disease and/or symptom of arthritis, wherein the ratio of CBD or CBDV to THC or THCV is smaller than or equal to 19:1.

Patent CN103826621A discloses a pharmaceutical composition including plant cannabinoid cannabidivarol (CBDV) and cannabidiol (CBD), the mass ratio of CBDV to CBD in this composition is 7:1 to 1:2, and this composition is used to treat neuropathy characterized by hyperexcitability, convulsion or epileptic seizure of a central nervous system.

Patent CN106074496A discloses application of hemp phenolic compounds in preparation of a drug for treating gout, and this prior art discloses application of hemp phenolic compounds in preparation of a drug for treating gout, decreasing blood uric acid, and treating hyperuricemia, wherein the content of cannabidiol is 0.3%-99.7%, the other ingredients are one or a mixture of several of tetrahydrocannabinol, cannabinol, cannabigerol, cannabicyclol, cannabinolic acid, tetrahydrocannabinolic acid, cannabidiolic acid, cannbigerolic acid, cannabidiolic acid, cannabinovarin, cannabidivarol, tetrahydrocannabinovarin, cannabichromene and cannabivarichromene.

Patent CN103533930A discloses cannabinoid compounds for treating neuropathic pains, and this prior art discloses application of cannabichromene, cannabigerol, cannabidivarol and/or tetrahydrocannabinol in treatment of neuropathic pains.

Patent CN038137291 discloses a film-shaped mucosal adherent dosage form for administering a hemp preparation, which mentioned that this preparation was able to treat and improve dysmenorrhea. This preparation includes at least one selected from the group consisting of tetrahydrocannabinol, cannabidiol, cannabinol, and cannabichrome.

Patent CN028059956 discloses a composition containing tetrahydrocannabinol (THC) and cannabidiol (CBD), wherein cannabinoid accounts for at least 80 wt % of the total weight, and the weight ratio of THC/CBD is 75:25-20:80, preferably 3:1-1:2, particularly preferably 2:1. The analgesic effect of this composition may also be used in treatment of chronic pains caused by diseases such as dysmenorrhea, except for advanced cancer or neurological diseases.

Patent US20160256411A1 discloses a method for treating a human disease condition or illness by applying a cannabinoid drug onto the neck back of a human patient, which includes treatment of dysmenorrhea.

Patent CN105031563A discloses a wine for dissipating blood stasis, wherein 240 parts of hemp kernel powder is added to 5000 parts of Baijiu to make a medicinal liquor, for use in treatment of dysmenorrhea.

Although a series of pharmaceutical compositions containing cannabidiol and/or cannabidivarol have been developed at present, existing compositions cannot meet the need of treatment for woman dysmenorrhea. For example, in oral drugs, CBD cannot be absorbed rapidly and is not released at a desired site; spray or aerosol usually contains irritant adjuvants, and meanwhile cannot achieve the purpose of continuous administration; in the traditional Chinese medicinal wine, alcohol may stimulate gastric mucosa and hurt a central nervous system of human, especially for underage women and women at a student stage, alcohol may influence physical development as well as study condition.

In order to overcome the shortcomings in the prior art, the present invention provide a composition which can prevent and/or treat woman dysmenorrhea, as well as a feminine hygiene product.

SUMMARY

The present invention overcomes the shortcoming of lackness of a composition of cannabidiol and/or cannabidivarol for effectively preventing and/or treating woman dysmenorrhea in the prior art, and provides an externally applied composition containing cannabidiol and/or cannabidivarol and a feminine hygiene product by adjustment of the content of cannabidiol and/or cannabidivarol in the composition as well as selection of a penetration enhancer.

A first aspect of the invention provides a composition for preventing and/or treating woman dysmenorrhea, wherein the composition includes cannabidiol and/or cannabidivarol, a penetration enhancer as well as a carrier.

The composition according to the present invention can merely contain cannabidiol or merely contain cannabidivarol, and can also contain both cannabidiol and cannabidivarol; a person skilled in the art can understand that, when the composition contains both cannabidiol and cannabidivarol, the mass ratio of the cannabidiol to the cannabidivarol can be any ratio, preferably the mass ratio of the cannabidiol to the cannabidivarol is (0.1-10):1, more preferably the mass ratio of the cannabidiol to the cannabidivarol is (2-8):1, especially preferably the mass ratio of the cannabidiol to the cannabidivarol is (3-7):1, most preferably the mass ratio of the cannabidiol to the cannabidivarol is (4-6):1.

The penetration enhancer according to the present invention is one or a combination of two or more selected from azone, volatile oil, 1,3-dimethyl-2-imidazolinone (DMI), propylene glycol, ethanol, and oleic acid, preferably azone.

The volatile oil according to the invention is a perfume oil obtained from plants, animals, microorganisms and derivatives thereof by distillation, squeezing or solvent extraction, preferably the volatile oil according to the present invention refers to a perfume oil obtained from a plant raw material by extraction, more preferably the volatile oil according to the present invention is obtained from Lamiaceae, such as peppermint, purple perilla, wrinkled giant hyssop, etc.; Apiaceae, such as fennel, radix angelicae sinensis, coriander, radix angelicae dahuricae, rhizoma chuanxiong, etc.; Compositae, such as argy wormwood leaves, herba artemisiae scopariae, rhizoma atractylodis, largehead atractylodes rhizomes, radix aucklandiae, etc.; Rutaceae, such as oranges, tangerines, Chinese prickly ash, etc.; Lauraceae, such as camphor tree, cinnamon, etc.; and Zingiberaceae, such as ginger, turmeric, radix curcumae, etc. by extraction. Particularly preferably, the volatile oil according to the present invention is ginger volatile oil or peppermint volatile oil.

Preferably, according to the present invention, the mass ratio of the cannabidiol and/or cannabidivarol to the penetration enhancer is 1:(0.1-0.8), more preferably the mass ratio of the cannabidiol and/or cannabidivarol to the penetration enhancer is 1:(0.1-0.5), most preferably the mass ratio of the cannabidiol and/or cannabidivarol to the penetration enhancer is 1:(0.2-0.4).

By comparing the compositions with a different ratio of the cannabidiol and/or cannabidivarol to the penetration enhancer, it is surprisingly found that when the ratio is within a specific range, the effects of improving dysmenorrhea by the cannabidiol and/or cannabidivarol are more outstanding, its reason may be due to improvement of a permeation effect of the penetration enhancer on skin absorption of a drug, meanwhile the penetration enhancer may influence cannabinoid receptors distributed in absorptive tissue. Further experiments indicate that, the penetration enhancers of different types may also influence treatment effects of the cannabidiol and/or cannabidivarol, especially azone is able to further enhance the effect of the cannabidiol and/or cannabidivarol.

The cannabidiol and/or cannabidivarol according to the present invention can be obtained by extraction or artificial synthesis.

Preferably, the cannabidiol and/or cannabidivarol according to the present invention are/is obtained from a hemp plant by extraction, the extraction site of the hemp plant may be one or a combination of any two and more of hemp seeds, hemp leaves, hemp flowers, hemp stalk cores, and hemp roots at any ratio, preferably the cannabidiol and/or cannabidivarol are/is obtained from the hemp flowers and hemp leaves by extraction.

Further, the cannabidiol and/or cannabidivarol may be a combination of cannabidiol and/or cannabidivarol obtained from different sites of a hemp plant by separate extraction, such as a combination of cannabidiol and/or cannabidivarol obtained from the hemp flowers by extraction and cannabidiol and/or cannabidivarol obtained from the hemp leaves by extraction; a combination of cannabidiol and/or cannabidivarol obtained from the hemp stalk cores by extraction, cannabidiol and/or cannabidivarol obtained from the hemp flowers by extraction and cannabidiol and/or cannabidivarol obtained from the hemp leaves by extraction, etc. The cannabidiol and/or cannabidivarol can also be obtained by combining different plant sites of the hemp plant, followed by simultaneous extraction, such as cannabidiol and/or cannabidivarol obtained from the hemp flowers and hemp leaves by extraction; cannabidiol and/or cannabidivarol obtained from the hemp stalk cores, hemp flowers and hemp leaves by extraction; cannabidiol and/or cannabidivarol obtained from the hemp stalk cores and hemp flowers by extraction; cannabidiol and/or cannabidivarol obtained from hemp stalk cores and hemp leaves by extraction; a combination of cannabidiol and/or cannabidivarol obtained from the hemp flowers and hemp leaves by extraction with cannabidiol and/or cannabidivarol obtained from the hemp leaves and hemp stalk cores by extraction, etc.

The cannabidiol and/or cannabidivarol according to the present invention may be prepared by a conventional plant extraction method in the prior art, such as a solvent extraction method, a water steam distillation method, a sublimation method, supercritical fluid extraction, a membrane separation and extraction technique, etc.; it is preferable to adopt solvent extraction, the extraction solvent may be alcohol with lower molecular weight (such as methanol, ethanol, butanol or propanol), acetate (such as methyl acetate or ethyl acetate), ketones (such as acetone), ethers (such as dimethyl ether or diethyl ether), aliphatic hydrocarbon or aromatic hydrocarbon or chlorinated hydrocarbon with low boiling point, etc.; the process of extraction may be heating reflux, and may also be combined with other extraction and separation methods such as one or a combination of more of extraction, distillation, crystallization, chromatographic separation, etc. for further purification and separation of the extract.

The composition according to the present invention can be in a form of liquid, gel, ointment or patch. Therefore, a person skilled in the art can understand that, the carrier according to the present invention may be any carrier suitable for the composition.

For example, when the composition is in a form of an ointment, the carrier is one or a combination of two or more selected from hexadecanol, vaseline, liquid paraffin, glyceryl monostearate, glycerol, ethylparaben, triethanolamine, ethylparaben, lanolin, and stearic acid.

When the composition is in a form of gel, the carrier is one or a combination of two or more selected from carbomer, polyvinyl alcohol, carboxymethyl cellulose and its sodium salt, and polyacrylic acid and its sodium salt.

When the composition is in a form of patch, the carrier is one or a combination of two or more selected from a hot-melt pressure sensitive adhesive, rubber, polymeric hydrogel, a medical adhesive tape and an acrylate pressure sensitive adhesive.

When the composition is a medial or hygienic product, the carrier can also be one or a combination of two or more of yarns, cotton threads, and hemp fiber.

When the composition is in a form of liquid, the carrier is one or a combination of two or more selected from an alcoholic solution such as an ethanol solution, glycerol, etc.; ethers, such as polyoxyethylene alkyl ether, etc.; esters, such as diester of dibasic acid; and vegetable oils, such as castor oil, and corn oil.

In one embodiment of the present invention, the carrier can also contain a binder, a filler, a humectant, a crosslinking agent, a coloring agent, a pH regulator, a tackifier, a preservative, etc. For example, the binder can be one or any combination of two or more selected from gelatin, sodium alginate, gum arabic, starch, methyl cellulose, carboxymethyl cellulose and its sodium salt, polyvinyl alcohol, polyethylene glycol, polyvinylpyrrolidone, carbomer, and polyacrylic acid and its sodium salt; the filler can be one or any combination of two or more selected from zinc oxide, colloidal silicon dioxide, calcium carbonate, diatomaceous earth, and titanium dioxide; the humectant can be any one or a combination of two or more selected from glycerol, propylene glycol, sorbitol, and polyethylene glycol; and the crosslinking agent can be any one or a combination of two or more selected from calcium hydroxide, aluminum trichloride, aluminum glycinate, and EDTA disodium.

In the composition according to the present invention, the ratio of the cannabidiol and/or cannabidivarol to the carrier can be selected on the basis of the specific preparation form. Preferably, the mass ratio of the cannabidiol and/or cannabidivarol to the carrier is 1:(4-50), preferably the mass ratio of the cannabidiol and/or cannabidivarol to the carrier is 1:(10-40), more preferably the mass ratio of the cannabidiol and/or cannabidivarol to the carrier is 1:(20-30).

The present invention also provides a feminine hygiene product, wherein the feminine hygiene product is made from the composition according to the present invention, the composition includes an active substance, a carrier and a penetration enhancer, the mass ratio of the active substance to the carrier is 1:(4-50), the mass ratio of the active substance to the penetration enhancer is 1:(0.1-0.8), the active substance is cannabidiol and/or cannabidivarol, the mass ratio of the cannabidiol to the cannabidivarol is (0.1-10):1, preferably the mass ratio of the cannabidiol to the cannabidivarol is (2-8):1, more preferably the mass ratio of the cannabidiol to the cannabidivarol is (3-7):1, especially preferably, the mass ratio of the cannabidiol to the cannabidivarol is (4-6):1. The carrier is one or a combination of two or more of yarns, cotton threads or hemp fiber. Preferably, in the composition, the carrier is hemp fiber, the hemp fiber is sprayed or impregnated with the active substance and penetration enhancer. More preferably, the feminine hygiene product is a sanitary towel, a sanitary napkin or a panty liner.

The present invention also provides application of a composition containing a cannabidiol and/or cannabidivarol in preparation of a drug for preventing and/or treating dysmenorrhea, wherein the composition includes cannabidiol and/or cannabidivarol, a penetration enhancer as well as a carrier; preferably the drug is an externally applied drug in a form of gel, ointment or patch, more preferably the drug is an externally applied drug in a form of ointment or patch, especially preferably the drug is an externally applied drug in a form of patch.

Dysmenorrhea according to the present invention is selected from primary dysmenorrheal and secondary dysmenorrhea.

Preventing and/or treating dysmenorrheal according to the present invention include/includes prevention and/or treatment of at least one or two or more symptoms selected from lower abdominal distention, nausea, vomiting, headache, diarrhea, narcolepsy, anorexia, impatience, lumbago, melosalgia, anemia, menometrorrhagia and taediumvitae which are caused by dysmenorrhea.

The present invention also provides a method for preventing and/or treating dysmenorrhea; the method includes administering a composition, and the composition includes cannabidiol and/or cannabidivarol, a penetration enhancer as well as a carrier.

Preferably, the composition includes cannabidiol and cannabidivarol, and the mass ratio of the cannabidiol to the cannabidivarol is (0.1-10):1.

Preferably, the mass ratio of the cannabidiol and/or cannabidivarol to the penetration enhancer is 1:(0.1-0.8).

In the present invention, the term "treatment" includes inhibition, delay, relief, weakening, restriction, alleviation or regression of disease, disorder, illness or condition, its occurrence and/or process, and/or its symptom.

According to the present invention, the term "prevention" includes decrease of the following risks: having, infection or experience of disease, disorder, illness or condition, its occurrence and/or process, and/or its symptom.

According to the present invention, the term "including" represents an "open" or "inclusive" term, thus they include the cited elements, they also allow to include additional and not mentioned elements.

DETAILED DESCRIPTION OF THE EMBODIMENTS

Example 1. Extraction of Cannabidiol (1) The raw materials hemp flowers, and leaves were washed to be clean and air dried;

(2) The above-mentioned air-dried raw materials were pulverized to 40-mesh;

(3) 95% ethanol with the amount being 8 times of the amount of the obtained powder was added into the obtained powder and cold extraction was conducted for 3 times, wherein cold extraction every time was conducted for 1 hour;

(4) Extracts were mixed, and decolored; and (5) Concentration was conducted under reduced pressure to a relative density of 1.05;

So as to obtain a cannabidiol extract, wherein the cannabidiol content, in percentage by mass, was 99.5%.

It should be noted that, description such as "the amount being 8 times" in the present invention means that the volume of the used extraction solvent is 8 times of the mass of the extraction site, for example, if the mass of the extraction site of hemp is 1 g, the volume of the extraction solvent is 8 ml.

Example 2. Extraction of Cannabidivarol (1) Raw materials hemp flowers and leaves were washed to be clean and air dried;

(2) The above-mentioned air-dried raw materials were pulverized to 40-mesh;

(3) Absolute ethyl alcohol with the amount being 10 times of the amount of the obtained powder was added into the obtained powder in a mass-to-volume ratio, and cold extraction was conducted for 3 times, wherein cold extraction every time was conducted for 1 hour;

(4) Extracts were mixed, decolored, and concentrated;

(5) A chromatographic column was taken, the column was packed by using silica gel as a filler, and the extract was loaded onto the column and passed through the column, wherein the mobile phase was 80:20 of petroleum ether and diethyl ether, and the flow rate was 3.0 ml/min; and (6) The eluate containing a cannabidivarol component was collected, and the solvent was removed by rotary evaporation to obtain a cannabidiol extract, wherein the cannabidivarol content (in mass percent) was 97.5%.

Example 3. Preparation of an Externally Applied Patch for Preventing and/or Treating Woman Dysmenorrhea An externally applied drug for preventing and/or treating woman dysmenorrhea was prepared, wherein the externally applied drug was an externally applied drug in a form of patch, a backing layer is made of nonwoven fabric, a protective layer is made of release paper, in the drug reservoir layer, the mass ratio of cannabidiol to the penetration enhancer is 1:0.5, the penetration enhancer is ginger volatile oil, the carrier of the drug reservoir layer is polymeric hydrogel, the mass ratio of the cannabidiol to the carrier is 1:4, and the polymeric hydrogel was prepared by mixing sodium carboxymethylcellulose, glycerol, water, aluminium oxide well at a mass ratio of 10:30:40:0.1.

Cannabidiol and ginger volatile oil were mixed well, and mixed with the polymeric hydrogel well, then the mixture was poured into a coater, the nonwoven fabric of the backing layer was evenly coated with the mixture, and the nonwoven fabric coated with the mixture was covered with the release paper of the protective layer to obtain the patch.

Example 4. Preparation of an Externally Applied Patch for Preventing and/or Treating Woman Dysmenorrhea An externally applied drug for preventing and/or treating woman dysmenorrhea was prepared, wherein the externally applied drug was an externally applied drug in a form of patch, a backing layer was made of nonwoven fabric, a protective layer was made of release paper, in the drug reservoir layer, the mass ratio of cannabidivarol to the penetration enhancer is 1:0.1, the penetration enhancer is peppermint volatile oil, the carrier of the drug reservoir layer was polymeric hydrogel, the mass ratio of the cannabidivarol to the carrier was 1:9, and the polymeric hydrogel was prepared by mixing sodium carboxymethylcellulose, propylene glycol, water, and calcium hydroxide well at a mass ratio of 7:25:30:0.2.

Cannabidivarol and peppermint volatile oil were mixed well, and mixed with the polymeric hydrogel well, then the mixture was poured into a coater, the nonwoven fabric of the backing layer was evenly coated with the mixture, and the nonwoven fabric coated with the mixture was covered with the release paper of the protective layer to obtain the patch.

Example 5. Preparation of an Externally Applied Patch for Preventing and/or Treating Woman Dysmenorrhea An externally applied drug for preventing and/or treating woman dysmenorrhea was prepared, wherein the externally applied drug was an externally applied drug in a form of patch, a backing layer was made of nonwoven fabric, a protective layer was made of release paper, in the drug reservoir layer, the mass ratio of cannabidiol to cannabidivarol was 5:1, the mass ratio of a mixture of the cannabidiol and cannabidivarol to the penetration enhancer was 1:0.8, the penetration enhancer is propylene glycol, the carrier of the drug reservoir layer was polymeric hydrogel, the mass ratio of the mixture of the cannabidiol and cannabidivarol to the carrier was 1:15, and the polymeric hydrogel was prepared by mixing sodium carboxymethylcellulose, glycerol, water, and calcium hydroxide well at a mass ratio of 8:40:55:0.3.

Cannabidiol and cannabidivarol were evenly mixed, and added into propylene glycol, stirred well, and then mixed with polymeric hydrogel well, then the mixture was poured into a coater, and the nonwoven fabric of the backing layer was evenly coated with the mixture, and the nonwoven fabric coated with the mixture was covered with the release paper of the protective layer to obtain the patch.

Example 6. Preparation of an Externally Applied Patch for Preventing and/or Treating Woman Dysmenorrhea An externally applied drug for preventing and/or treating woman dysmenorrhea was prepared, wherein the externally applied drug was an externally applied drug in a form of patch, a backing layer was made of nonwoven fabric, a protective layer was made of release paper, in the drug reservoir layer, the mass ratio of cannabidivarol to the penetration enhancer was 1:0.5, the penetration enhancer was azone, the carrier of the drug reservoir layer was a hot-melt pressure sensitive adhesive, the mass ratio of cannabidivarol to the carrier was 1:20, and the hot-melt pressure sensitive adhesive was prepared by weighing styrene-butadiene rubber, a tackifier (the tackifier is a mixture of glycerol ester of hydrogenated rosin with pentaerythritol ester of rosin at a mass ratio of 1:1) and squalane at a mass ratio of 2.8:3.3:2.1, conducting heating to melt the weighed materials, and conducting uniform mixing.

Cannabidivarol and azone were mixed well, and mixed with the hot-melt pressure sensitive adhesive well, then the mixture was poured into a coater, and the nonwoven fabric of the backing layer was evenly coated with the mixture, and the nonwoven fabric coated with the mixture was covered with the release paper of the protective layer to obtain the patch.

Example 7. Preparation of an Externally Applied Patch for Preventing and/or Treating Woman Dysmenorrhea An externally applied drug for preventing and/or treating woman dysmenorrhea was prepared, wherein the externally applied drug was an externally applied drug in a form of patch, a backing layer was made of nonwoven fabric, a protective layer was made of release paper, in the drug reservoir layer, the mass ratio of cannabidiol to the penetration enhancer was 1:0.1, the penetration enhancer was azone, the carrier of the drug reservoir layer is a hot-melt pressure sensitive adhesive, the mass ratio of cannabidiol to the carrier was 1:25, and the hot-melt pressure sensitive adhesive was prepared by weighing styrene-butadiene rubber, a tackifier (the tackifier was a mixture of glycerol ester of hydrogenated rosin and pentaerythritol ester of rosin at a mass ratio of 1:1) and squalane at a mass ratio of 3.9:3.3:2.4, conducting heating to melt the weighed materials, and conducting uniform mixing.

Cannabidiol and azone were mixed well, and mixed with the hot-melt pressure sensitive adhesive well, then the mixture was poured into a coater, and the nonwoven fabric of the backing layer was evenly coated with the mixture, and the nonwoven fabric coated with the mixture was covered with the release paper of the protective layer to obtain the patch.

Example 8. Preparation of an Externally Applied Patch for Preventing and/or Treating Woman Dysmenorrhea An externally applied drug for preventing and/or treating woman dysmenorrhea was prepared, wherein the externally applied drug was an externally applied drug in a form of patch, a backing layer was made of nonwoven fabric, a protective layer was made of release paper, in the drug reservoir layer, the mass ratio of drug cannabidiol to the penetration enhancer is 1:0.8, the penetration enhancer was azone, the carrier of the drug reservoir layer was a hot-melt pressure sensitive adhesive, the mass ratio of cannabidiol to the carrier was 1:30, and the hot-melt pressure sensitive adhesive was prepared by weighing styrene-butadiene rubber, a tackifier (the tackifier is a mixture of glycerol ester of hydrogenated rosin and pentaerythritol ester of rosin at a mass ratio of 1:1) and squalane at a mass ratio of 3.5:4.7:3.5, conducting heating to melt the weighed materials, and conducting uniform mixing.

Cannabidiol and azone were mixed well, and mixed with the hot-melt pressure sensitive adhesive, then the mixture was poured into a coater, and the nonwoven fabric of the backing layer was evenly coated with the mixture, and the nonwoven fabric coated with the mixture was covered with the release paper of the protective layer to obtain the patch.

Example 9. Preparation of a Composition for Preventing and/or Treating Woman Dysmenorrhea and Using Hemp Fiber as a Carrier Preparation of a composition for preventing and/or treating woman dysmenorrhea was provided, wherein the carrier of the composition was hemp fiber, in the composition, the mass ratio of cannabidiol to the carrier was 1:50, in the composition, the penetration enhancer was azone, and the mass ratio of cannabidiol to azone is 1:0.8.

Appropriate amount of ethanol was taken, and cannabidiol was dissolved in ethanol, and azone was added into ethanol, the above materials were stirred well, and hemp fiber was immersed in ethanol in which cannabidiol and azone were dissolved, the materials were allowed to stand for 1 hour, and the hemp fiber was taken out from ethanol, and air-dried in an aseptic environment at 16° C. for 3 hours, and the above-mentioned steps were repeated until ethanol was entirely immersed into the hemp fiber to obtain the composition.

Example 10. Preparation of a Sanitary Towel for Preventing and/or Treating Woman Dysmenorrhea (1) Preparation of a composition for preventing and/or treating woman dysmenorrhea was provided, wherein the carrier of the composition is hemp fiber, in the composition, the mass ratio of cannabidiol to the carrier is 1:45, in the composition, the penetration enhancer is azone, and the mass ratio of cannabidiol to azone is 1:0.7. Appropriate amount of ethanol was taken, and cannabidiol was dissolved in ethanol, and azone was added into ethanol, the above materials were stirred well, and the hemp fiber was immersed in ethanol in which cannabidiol and azone were dissolved, the materials were allowed to stand for 1 hour, and the hemp fiber was taken out from ethanol, and air dried at 16° C. in an aseptic environment for 3 hours, and the above-mentioned steps were repeated until ethanol was entirely immersed into the hemp fiber to obtain the composition.

(2) A sanitary towel was prepared by using the composition containing hemp fiber prepared in the step (1), the sanitary towel was composed of an outer layer, an inner layer and an lower layer, the outer layer was made by weaving the composition containing hemp fiber prepared in the step (1), the inner layer of the sanitary towel was made of a cotton material, and the lower layer was made of a film material.

Example 11. Preparation of an Externally Applied Cream for Preventing and/or Treating Woman Dysmenorrhea An externally applied drug for preventing and/or treating woman dysmenorrhea was prepared, wherein the externally applied drug was a cream, in the cream, the mass ratio of cannabidiol to the penetration enhancer was 1:0.3, the penetration enhancer was ginger volatile oil, in the carrier, the oil phase was a mixture of lanolin, stearic acid, and liquid paraffin at a mass ratio of 1.6:2.5:1.8, in the carrier, the water phase was a mixture of glycerol, ethylparaben, carbomer at a mass ratio of 7.3:1:1, and the mass ratio of cannabidiol to the carrier was 1:40.

Lanolin, stearic acid, and liquid paraffin were mixed well, heated to 65° C.-90° C., and fully dissolved to obtain an oil phase; glycerol, ethylparaben, carbomer and a part of water were mixed and heated to 65° C.-90° C. to obtain a water phase; the oil phase was added into the water phase, and stirred to obtain a cream carrier, and cannabidiol was added into the cream carrier, and stirred well, and the ginger volatile oil was added into the cream, and stirred well to obtain the externally applied cream.

Example 12. Preparation of an Externally Applied Cream for Preventing and/or Treating Woman Dysmenorrhea An externally applied drug for preventing and/or treating woman dysmenorrhea was prepared, wherein the externally applied drug was a cream, in the cream, the mass ratio of cannabidiol to the penetration enhancer was 1:0.5, the penetration enhancer was peppermint volatile oil, in the carrier, the oil phase was a mixture of vaseline, triethanolamine, stearic acid, and liquid paraffin at a mass ratio of 2:1.2:2.8:1.9, in the carrier, the water phase was a mixture of glycerol, ethylparaben, and carbomer at a mass ratio of 8:1.5:1.7, and the mass ratio of cannabidiol to the carrier was 1:50.

Vaseline, triethanolamine, stearic acid, and liquid paraffin were mixed well, heated to 65° C.-90° C. and totally dissolved to obtain an oil phase; glycerol, ethylparaben, carbomer and a part of water were mixed and heated to 65° C.-90° C. to obtain a water phase; the oil phase was added into the water phase, and stirred to obtain a cream carrier, and cannabidiol was added into the cream carrier, and stirred well, and the peppermint volatile oil was added into the cream, and stirred well to obtain the externally applied cream.

Example 13. Preparation of an Externally Applied Liquid Liniment for Preventing and/or Treating Woman Dysmenorrhea An externally applied drug for preventing and/or treating woman dysmenorrhea was prepared, wherein the externally applied drug was a liquid externally applied drug, in the liquid externally applied drug, the mass ratio of cannabidiol to the penetration enhancer was 1:0.8, the penetration enhancer was azone, the carrier was a mixture of glycerol and ethanol at a mass ratio of 1:1, and the mass ratio of the cannabidiol to the carrier was 1:50.

Cannabidiol was dissolved in a mixed liquor of glycerol and ethanol, and stirred well, then azone was added and stirred until a colorless and transparent liquid was formed to obtain a body surface externally applied liquid liniment.

Example 14. Influence of Compositions with Different Cannabidiol or Cannabidivarol Contents on a Rat Dysmenorrhea Model Experiment samples: patches containing cannabidiol and azone and the carrier at a mass ratio of 1:0.8:4, 1:0.8:25, and 1:0.8:50; patches containing cannabidivarol and azone and the carrier at a mass ratio of 1:0.8:4, 1:0.8:25, and 1:0.8:50.

Experimental animals: female rats of 200-220 g.

Experiment method: the patches containing cannabidiol or cannabidivarol and azone and the carrier at mass ratio of 1:0.8:4, 1:0.8:25, and 1:0.8:50 were cut into small patches of 3×3 $cm^2$ ready for use, wherein in the patches of each group, the total dose of the composition of cannabidiol or cannabidivarol, azone and the carrier were the same.

70 healthy adult female rats were taken, the body weight was 210 g±8 g, and the rats were randomly divided into 7 groups, and the hairs on abdominal skin were shaved.

The first group was a negative control group, in the rat abdomen patch, the composition containing cannabidiol or cannabidivarol, azone and the carrier was replaced with equal quantity of physiological saline;

In the second group, in the rat abdomen patch, the mass ratio of cannabidiol to azone to the carrier was 1:0.8:4;

In the third group, in the rat abdomen patch, the mass ratio of cannabidiol to azone to the carrier was 1:0.8:25;

In the fourth group, in the rat abdomen patch, the mass ratio of cannabidiol to azone to the carrier was 1:0.8:50;

In the fifth group, in the rat abdomen patch, the mass ratio of cannabidivarin to azone to the carrier was 1:0.8:4;

In the sixth group, in the rat abdomen patch, the mass ratio of cannabidivarol to azone to the carrier was 1:0.8:25;

In the seventh group, in the rat abdomen patch, the mass ratio of cannabidivarol to azone to the carrier was 1:0.8:50. The patch was changed every day, and continued to be applied for 4 days.

The rats in each group were respectively injected subcutaneously (sc) with diethylstilbestrol, and subcutaneous injection was continued to be conducted for 4 days, and the daily dose was 8 mg/kg, so as to increase sensitivity of uteruses. In each group, on the 4th day, after 2 hours of administration, the rats were injected intraperitoneally with oxytocin at a dose of 2 IU/rat, to make rat uteruses shrink, and induce their writhing responses, the writhing number of every rat within subsequent 40 minutes was observed and recorded, and incidences of writhing were calculated. The recorded results were as shown in Table 1.

Wherein, incidence of writhing (%)=writhing animal number in each group/experimental animal number in each group×100%.

Experiment Results:

As shown in Table 1, the patches in the second to the seventh groups had obvious relieving effects on rat dysmenorrhea-like response induced by oxytocin; the higher the content of cannabidiol or cannabidivarol, the more significant the patches were able to relieve the writhing response in rats, and the longer the response latency can be prolonged.

TABLE 1

Results of the rat writhing experiment using compositions with different cannabidiol or cannabidivarol contents.

| Groups | Animal number/group | Writhing number within 40 minutes | Incidence of writhing (%) |
| --- | --- | --- | --- |
| First group | 10 | 38.39 ± 11.03 | 100 |
| Second group | 10 | 9.64 ± 11.69 | 30 |
| Third group | 10 | 13.43 ± 9.65 | 50 |
| Fourth group | 10 | 16.73 ± 12.17 | 60 |
| Fifth group | 10 | 14.34 ± 10.73 | 40 |
| Sixth group | 10 | 17.22 ± 11.98 | 60 |
| Seventh group | 10 | 18.76 ± 10.91 | 60 |

Example 15. Influence of a Ratio of Cannabidiol to the Penetration Enhancer on Rat Dysmenorrhea Model Experiment samples: patches containing cannabidiol and azone at a mass ratio of 1:1, 1:0.8, 1:0.4, 1:0.1, and 1:0.05.

Experimental animals: female rats of 200-220 g.

Experiment method: patches containing cannabidiol and azone at a mass ratio of 1:1, 1:0.8, 1:0.4, 1:0.1, and 1:0.05 were cut into small patches of 3×3 $cm^2$ ready for use, wherein in the patches of each group, the dose of cannabidiol were the same, and the mass ratio of cannabidiol to the carrier were all 1:10.

60 female rats with a body weight of 200-220 g were randomly divided into 6 groups, 10 rats in every group, and the hairs on abdominal skin were shaved.

The first group was a negative control group, the rat abdomens were applied with patches of 3×3 $cm^2$, wherein the patch prepared from a mixture of cannabidiol and azone was replaced with equal quantity of physiological saline;

In a second group, the rat abdomens were applied with patches containing cannabidiol and azone at a mass ratio of 1:1;

In a third group, the rat abdomens were applied with patches containing cannabidiol and azone at a mass ratio of 1:0.8;

In a fourth group, the rat abdomens were applied with patches containing cannabidiol and azone at a mass ratio of 1:0.4;

In a fifth group, the rat abdomens were applied with patches containing cannabidiol and azone at a mass ratio of 1:0.1;

In a sixth group, the rat abdomens were applied with patches containing cannabidiol and azone at a mass ratio of 1:0.05.

The patches were changed every day, and continued to be applied for 4 days.

The rats in each group were respectively injected subcutaneously (sc) with diethylstilbestrol, and subcutaneous injection was continued to be conducted for 4 days, and the daily dose was 8 mg/kg, so as to increase sensitivity of uteruses. In each group, at the 4th day, after 2 h of administration, the rats were injected intraperitoneally with oxytocin at a dose of 2 IU/rat, to make the rat uteruses shrink, and induce their writhing responses, the writhing number of every rat within the subsequent 40 minutes was observed and recorded, and incidence of writhing was calculated. The recorded results were as shown in Table 2.

Wherein, incidence of writhing (%)=writhing animal number in each group/experimental animal number in each group×100%.

Experiment Results:

As the results shown in Table 2, compared with the negative control group, the other groups had the advantages that the patches containing the mixture of cannabidiol and azone were all able to relieve the writhing response of the rats, especially the patches in the third group, the fourth group, and the fifth group were more able to significantly relieve the writhing response of the rats, which showed that when the mass ratio of cannabidiol to azone was 1:0.8, 1:0.4, and 1:0.1, the patches were able to better relieve dysmenorrhea of the rats.

TABLE 2

Experiment results of rat writhing experiment using the compositions with different penetration enhancer contents.

| Groups | Writhing number within 40 minutes | Incidence of writhing (%) |
| --- | --- | --- |
| First group | 38.39 ± 11.03 | 100 |
| Second group | 22.85 ± 10.34 | 70 |
| Third group | 13.43 ± 9.65 | 50 |
| Fourth group | 10.62 ± 9.42 | 40 |
| Fifth group | 11.12 ± 10.35 | 40 |
| Sixth group | 26.96 ± 10.71 | 70 |

Example 16. Influence of the Type of the Penetration Enhancer on Rat Dysmenorrhea Model Experiment samples: a patch with a mass ratio of cannabidiol to azone being 1:0.8; a patch with a mass ratio of cannabidiol to ginger volatile oil being 1:0.8; a patch with a mass ratio of cannabidiol to peppermint volatile oil being 1:0.8; a patch with a mass ratio of cannabidiol to DMI being 1:0.8.

Experimental animals: female rats of 200-220 g.

Experiment Method:

The patch containing cannabidiol and azone at a mass ratio of 1:0.8; the patch containing cannabidiol and ginger volatile oil at a mass ratio of 1:0.8; the patch containing cannabidiol and peppermint volatile oil at a mass ratio of 1:0.8; and the patch containing cannabidiol and DMI at a mass ratio of 1:0.8 were cut into small patches of 3×3 cm$^2$ ready for use, wherein in the patches of each group, the doses of cannabidiol were the same, and the mass ratio of cannabidiol to the carrier were all 1:10.

50 female rats with a body weight of 200-220 g were randomly divided into 5 groups, 10 rats in every group, and the hairs on abdominal skin were shaved.

The first group was a negative control group, the rat abdomens were applied with patches of 3×3 cm$^2$, wherein the patch prepared from a mixture of cannabidiol and the penetration enhancer was replaced with equal amount of physiological saline;

In the second group, the rat abdomens were applied with patches containing cannabidiol and azone at a mass ratio of 1:0.8;

In the third group, the rat abdomens were applied with patches containing cannabidiol and ginger volatile oil at a mass ratio of 1:0.8;

In the fourth group, the rat abdomens were applied with patches containing cannabidiol and peppermint volatile oil at a mass ratio of 1:0.8;

In the fifth group, the rat abdomens were applied with patches containing cannabidiol and DMI at a mass ratio of 1:0.8.

The patches were changed every day, and continued to be applied for 4 days.

The rats in each group were respectively subcutaneously injected (sc) with diethylstilbestrol, and subcutaneous injection was continued to be conducted for 4 days, and the daily dose was 8 mg/kg (in terms of cannabidiol), so as to increase sensitivity of uteruses. In each group, on the 4th day, after 2 hours of administration, the rats were injected intraperitoneally with oxytocin at a dose of 2 IU/rat, to make the rat uteruses shrink, and induce their writhing responses, the writhing number of every rat within subsequent 40 minutes was observed and recorded, and incidence of writhing was calculated. Results are as shown in Table 3, wherein incidence of writhing (%)=writhing animal number in each group/experimental animal number in each group×100%.

Experiment Results:

As the results shown in Table 3, compared with the negative control group, the other groups had the advantages that the patches containing a mixture of cannabidiol and the penetration enhancer were able to significantly relieve the writhing response of the rats, especially the patches in the second group were able to more significantly relieve the writhing response of the rats, which showed that the patches prepared from cannabidiol and azone were able to better relieve dysmenorrhea of the rats.

TABLE 3

Experiment results of the rat writhing experiment using different types of penetration enhancers.

| Groups | Writhing number within 40 minutes | Incidence of writhing (%) |
| --- | --- | --- |
| First group | 38.39 ± 11.03 | 100 |
| Second group | 13.43 ± 9.65 | 40 |
| Third group | 16.87 ± 10.35 | 50 |
| Fourth group | 17.69 ± 9.28 | 60 |
| Fifth group | 16.17 ± 9.59 | 50 |

Example 17. Influence of a Content Ratio of Cannabidiol to Cannabidivarol in the Composition on Rat Dysmenorrhea Model Experiment samples: patches containing cannabidiol, cannabidivarol, azone and the carrier, in the patches, the mass ratio of cannabidiol and cannabidivarol to azone to the carrier was 1:0.8:10, and in each group, the mass ratio of cannabidiol to cannabidivarol were 1:0.1, 1:0.2, 1:1, and 1:10, respectively.

Experimental animals: female rats of 200-220 g.

Experiment Method:

The patches of each group in which the mass ratio of cannabidiol to cannabidivarol in the composition was 1:0.1, 1:0.2, 1:1, and 1:10, respectively were cut into small patches of 3×3 cm$^2$ ready for use, wherein in the patches of each group, the total dose of cannabidiol and cannabidivarol was the same.

40 female rats with a body weight of 200-220 g were randomly divided into 4 groups, 10 rats in every group, and the hairs on abdominal skin were shaved.

In the first group, the rat abdomens were applied with patches containing cannabidiol and cannabidivarol with a mass ratio of 1:0.1;

In the second group, the rat abdomens were applied with patches containing cannabidiol and cannabidivarol with a mass ratio of 1:0.2;

In the third group, the rat abdomens were applied with patches containing cannabidiol and cannabidivarol with a mass ratio of 1:1;

In fourth group, the rat abdomens were applied with patches containing cannabidiol and cannabidivarol with a mass ratio of 1:10.

The patches were changed every day, and continued to be applied for 4 days.

The rats in each group were respectively injected subcutaneously (sc) with diethylstilbestrol, and subcutaneous injection was continued to be conducted for 4 days, and the daily dose was 8 mg·kg-1 (in terms of cannabidiol), so as to increase sensitivity of uteruses. In each group, on the 4th day, after 2 hours of administration, the rats were injected intraperitoneally with oxytocin at a dose of 2 IU/rat, to make the rat uteruses shrink, and induce their writhing responses, the writhing number of each rat within subsequent 40 minutes was observed and recorded, and incidence of writhing was calculated. The results are as shown in Table 4, wherein incidence of writhing (%)=writhing animal number in each group/experimental animal number in each group× 100%.

Experiment Results:

As the results shown in Table 4, the patches containing cannabidiol and cannabidivarol at different ratios have obvious relieving effects on the rat dysmenorrhea-like response caused by oxytocin, but when the content ratio of cannabidiol in composition is higher, the patches were more able to relieve the writhing response of the rats, especially when the mass ratio of cannabidiol and cannabidivarol is 1:0.2, the patches have the best effect.

TABLE 4

Experiment results of the rat writhing experiment using compositions containing cannabidiol and cannabidivarol at a different ratio.

| Groups | Writhing number within 40 minutes | Incidence of writhing (%) |
| --- | --- | --- |
| First group | 14.18 ± 10.32 | 40 |
| Second group | 12.79 ± 11.98 | 40 |
| Third group | 15.47 ± 12.98 | 50 |
| Fourth group | 16.08 ± 10.55 | 50 |

The above-mentioned examples do not limit the present invention in any way, the technical solutions obtained in a manner of equivalent substitution or equivalent alternation all fall in the protection scope of the invention.

The invention claimed is:

1. A feminine hygiene product comprising a composition for treating dysmenorrhea, wherein the composition comprises cannabidiol and cannabidivarol, a penetration enhancer and a carrier, wherein a mass ratio of cannabidiol to cannabidivarol is (0.1-10):1.

2. The feminine hygiene product comprising the composition for treating dysmenorrhea according to claim 1, wherein the penetration enhancer is azone.

3. The feminine hygiene product comprising the composition for treating dysmenorrhea according to claim 1, wherein the mass ratio of the cannabidiol and/or cannabidivarol to the penetration enhancer is 1:(0.1-0.8).

4. The feminine hygiene product comprising the composition for treating dysmenorrhea according to claim 1, wherein the cannabidiol and cannabidivarol is extracted from a hemp plant, and the extraction site of the hemp plant is one or a combination of any two and more of hemp seeds, hemp leaves, hemp flowers, hemp stalk cores, and hemp roots at any ratio.

5. The feminine hygiene product comprising the composition for treating dysmenorrhea according to claim 1, wherein the composition is in a form of liquid, gel, ointment or patch.

6. The feminine hygiene product comprising the composition for treating dysmenorrhea according to claim 1,
wherein the carrier is one or a combination of two or more selected from yarns, cotton threads or hemp fiber.

7. The feminine hygiene product comprising the composition for treating dysmenorrhea according to claim 1, wherein the carrier also contains one or a combination of two or more of a binder, a filler, a humectant, a crosslinking agent, a coloring agent, a pH regulator, and a preservative.

8. The feminine hygiene product comprising the composition for treating dysmenorrheal according to claim 7, wherein the binder is one or any combination of two or more selected from gelatin, sodium alginate, gum arabic, starch, methyl cellulose, carboxymethyl cellulose and its sodium salt, polyvinyl alcohol, polyethylene glycol, polyvinylpyrrolidone, carbomer, and polyacrylic acid and its sodium salt; the filler is one or any combination of two or more selected from zinc oxide, colloidal silicon dioxide, calcium carbonate, diatomaceous earth, and titanium dioxide; the humectant is any one or a combination of two or more selected from glycerol, propylene glycol, sorbitol, and polyethylene glycol; and the crosslinking agent is any one or a combination of two or more selected from calcium hydroxide, aluminum trichloride, aluminum glycinate, and EDTA disodium.

9. The feminine hygiene product comprising the composition for treating dysmenorrheal according to claim 1, wherein the mass ratio of the cannabidiol and/or cannabidivarol to the carrier in the composition is 1:(4-50).

10. The feminine hygiene product according to claim 1, wherein the feminine hygiene product is a sanitary towel, a sanitary napkin or a panty liner.

11. A method for treating dysmenorrhea using a feminine hygiene product for treating dysmenorrhea, wherein the method comprises applying a composition comprising cannabidiol and cannabidivarol, a penetration enhancer and a carrier, wherein a mass ratio of cannabidiol to cannabidivarol is (0.1-10):1, and a carrier comprising one or more of yarns, cotton threads or hemp fiber.

12. The method for treating dysmenorrhea using a feminine hygiene product according to claim 11, wherein the the mass ratio of the cannabidiol to the cannabidivarol is (0.1-10):1.

13. The method for treating dysmenorrheal using a feminine hygiene product according to claim 11, wherein the mass ratio of the cannabidiol and cannabidivarol to the penetration enhancer is 1:(0.1-0.8).

* * * * *